(12) United States Patent
Li et al.

(10) Patent No.: US 9,056,823 B2
(45) Date of Patent: Jun. 16, 2015

(54) USE OF ORGANIC FRAMEWORK POROUS SOLID ACID

(75) Inventors: Wenpeng Li, Beijing (CN); Fengshou Xiao, Beijing (CN); Haicheng Xiao, Beijing (CN); Fujian Liu, Beijing (CN); Yinghui Li, Beijing (CN); Xiangju Meng, Beijing (CN); Xianming Xu, Beijing (CN); Xiangmin Yu, Beijing (CN); Wei Zhang, Beijing (CN); Kezhong Xu, Beijing (CN); Guoquan Song, Beijing (CN); Haotian Pei, Beijing (CN); Fangwei Li, Beijing (CN); Qunying Zeng, Beijing (CN); Zhixiang Zhang, Beijing (CN); Yueman Li, Beijing (CN)

(73) Assignee: PetroChina Company Limited, Beijing (CN)

( * ) Notice: Subject to any disclaimer, the term of this patent is extended or adjusted under 35 U.S.C. 154(b) by 0 days.

(21) Appl. No.: 14/131,496

(22) PCT Filed: Jul. 6, 2012

(86) PCT No.: PCT/CN2012/000938
§ 371 (c)(1),
(2), (4) Date: Mar. 27, 2014

(87) PCT Pub. No.: WO2013/007103
PCT Pub. Date: Jan. 17, 2013

(65) Prior Publication Data
US 2014/0235891 A1     Aug. 21, 2014

(30) Foreign Application Priority Data
Jul. 8, 2011 (CN) .......................... 2011 1 0191278

(51) Int. Cl.
| | | |
|---|---|---|
| C07C 67/08 | (2006.01) | |
| C07C 45/65 | (2006.01) | |
| B01J 31/10 | (2006.01) | |
| B01J 37/10 | (2006.01) | |
| C07C 45/46 | (2006.01) | |
| C08F 112/36 | (2006.01) | |
| C08F 8/36 | (2006.01) | |
| B01J 27/055 | (2006.01) | |
| B01J 35/02 | (2006.01) | |
| B01J 37/00 | (2006.01) | |

(52) U.S. Cl.
CPC ................. *C07C 45/65* (2013.01); *B01J 31/10* (2013.01); *C07C 67/08* (2013.01); *C07C 45/46* (2013.01); *C08F 112/36* (2013.01); *C08F 8/36* (2013.01); *B01J 37/10* (2013.01); *B01J 27/055* (2013.01); *B01J 35/023* (2013.01); *B01J 37/0036* (2013.01); *C07C 2101/14* (2013.01)

(58) Field of Classification Search
CPC .................................. B01J 31/10; B01J 37/10
USPC ........ 560/265, 231, 129; 568/315; 521/50, 61
See application file for complete search history.

(56) References Cited

FOREIGN PATENT DOCUMENTS

| | | | |
|---|---|---|---|
| CN | 101143911 A | | 3/2008 |
| CN | 101143911 A | * | 3/2008 |
| CN | 101864019 A | | 10/2010 |

OTHER PUBLICATIONS

English Tranlsation of CN 101864019A from LexisNexis Total Patent, Mar. 26, 2014.
English Tranlsation of CN 101143911A from LexisNexis Total Patent, Mar. 26, 2014.

* cited by examiner

*Primary Examiner* — Yong Chu
(74) *Attorney, Agent, or Firm* — Woodard, Emhardt, Moriarty, McNett & Henry LLP

(57) ABSTRACT

The invention relates to a catalyst for the catalytic esterification and acylation reaction. The catalyst is prepared by the steps of adding a divinyl benzene monomer into a solvent prepared by mixing azobisisobutyronitrile, tetrahydrofuran and water, performing hydrothermal treatment at the normal temperature under the constant pressure, and volatilizing the solvent at the room temperature to obtain polydivinylbenzene; grinding the polydivinylbenzene into 200-mesh powder and performing degassing treatment under the nitrogen condition; adding polydivinylbenzene blocks into 1,1',2-trichloroethane to explode and crack into small blocks, wherein the small blocks swell; evenly mixing 1,1',2-trichloroethane and concentrated sulfuric acid, adding silver sulfate serving as a catalyst, adding processed polydivinylbenzene, performing sulfonation, filtering and washing with dioxane and water till it is neutral, performing drying, using dilute sulphuric acid to activate, performing washing till the it is neutral and performing drying. The catalyst has high catalytic activity and conversion rate.

10 Claims, No Drawings

USE OF ORGANIC FRAMEWORK POROUS SOLID ACID

REFERENCE TO RELATED APPLICATIONS

This application is a U.S. national stage of PCT/CN2012/000938, filed on 6 Jul. 2012, which claims priority from Chinese patent application No. 201110191278.8, filed on 8 Jul. 2011. The entire contents of both of those applications are hereby incorporated into this application by reference.

FIELD OF THE INVENTION

The present invention relates to an application of organic framework porous solid acid.

BACKGROUND TO THE INVENTION

Solid acid is widely used as the development of chemistry industry, especially plays a very important role in the field of petrochemicals and fine chemicals. Traditional acid catalysts comprise zeolite molecular sieve, vulcanized metal oxides, acid-functionalized mesoporous materials, heteropolyacids and so on, but the defects of which, such as hydrophilic framework structure, the pore size limitation of zeolite material and the like, affect the wide application of inorganic solid acid material. Compared to the acid catalyst with traditional inorganic framework, pure organic framework solid acid materials get more and more widely studied for unique framework hydrophobic property, simple and convenient functionalizing process and better catalytic property.

It is known that a strong acidic cation resin, with divinyl benzene and styrene copolymer as its framework, and sulfonate as active functional group, may be used as a new type of organic framework solid acid material. The hydrophobic framework structure and high acid site content of the strong acidic cation resin make it possible to be used in the fields of acid catalytic reaction and ion exchange, comprising esterification, ester exchange and etherification, with very good results (*J. Catal.* 2008, Vol. 254, p. 205.). And industrialization of that has been achieved nowadays, and plays a very important role in the industrial application. However, the defects, such as low specific surface area, poor porous structure and framework with poor stability, limit its application in various fields.

SUMMARY OF THE INVENTION

One objective of the present invention is to provide an application of organic framework porous solid acid, in which porous poly divinyl benzene is used as material for good swelling property, the organic framework obtained from sulfonation reaction solid acid is used for the catalyst of catalytic esterification and acylation reaction It has advantages of high crosslinking degree, high stability, and has large specific surface area and various porous structures.

A synthetic method of organic framework porous solid acid according to the invention comprises:

(1) 2 g divinyl benzene (DVB) monomer is added into a mixture solvent comprising 0.03-0.05 g azobisisobutyronitrile, 10-20 ml tetrahydrofuran and 1-2 ml water, which is stirred for more than 3 hours at ambient temperature and pressure followed by hydrothermal treatment for 1-2 days at 75-150° C., then the obtained product is taken out, opened and volatilized at the room temperature to obtain polydivinylbenzene (PDVB) having high specific surface area and various mesoporous structures;

(2) 2-3 g polydivinylbenzene (PDVB) is ground into 200-mesh powder and degassed for 10 h under nitrogen condition for 10 h;

(3) 2.0 g polydivinylbenzene (PDVB) blocks are added into 1,1',2-trichloroethane, then PDVB material rapidly swells, explodes and cracks into small blocks accompanied by rapid volume expansion of PDVB;

(4) 30 milliliter 1,1',2-trichloroethane is mixed homogenously with 70 mL concentrated sulphuric acid having a mass concentration of 98%, with silver sulfate being added as a catalyst, the mixture is then stirred uniformly followed by adding processed polydivinylbenzene (PDVB) obtained from (3) with severe agitation, and the temperature of sulfonation is increased to 90° C. for 12 h, the product is filtered and washed with dioxane and then washed with water till neutral, dried at 80° C., subsequently activated by 0.1M dilute sulphuric acid for 4 hours, then washed with quantity of water till neutral, finally dried and at ready.

DESCRIPTION OF THE PREFERRED EMBODIMENTS

A synthetic method of novel solid acid material according to the invention, having efficient stable structure, high specific surface area, high sulfonate content, is demonstrated in detail with examples as follows.

In the examples, the sample name consists of two parts: the PDVB represents mesoporous polydivinylbenzene, and "—$SO_3H$" represents sulfonate functionalized mesoporous polydivinylbenzene material.

Example 1

The mesoporous polydivinylbenzene material, i.e. PDVB, is firstly synthesized by a mixture solvent of tetrahydrofuran and water.

2 g DVB monomer is added into a mixture solvent comprising 0.03-0.05 g azobisisobutyronitrile, 10-20 ml tetrahydrofuran and 1-2 ml water, which is stirred for more than 3 hours at ambient temperature and pressure followed by hydrothermal treatment for 1-2 days at 75-150° C., then the obtained product is taken out, opened and volatilized at the room temperature to obtain polydivinylbenzene (PDVB) having high specific surface area and various mesoporous structures.

Example 2

Sulfonation reaction is carried out with dichloromethane as solvent and concentrated sulphuric acid as sulfonation agent.

(1) 2-3 g PDVB is ground into ultrafine powder which is then degassed for 10 h at 100-150° C. under nitrogen condition;

(2) swelling process: 2.0 g PDVB blocks are added into excessive solvent, PDVB material rapidly swells, explodes and cracks into small blocks accompanied by rapid volume expansion;

(3) 30 milliliter dichloromethane is mixed homogenously with 70 mL concentrated sulfuric acid with 0.2 g silver sulfate being added as a catalyst and agitating uniformly, the mixture is then mixed homogenously, and the said PDVB followed is added followed by severe agitation, and then the temperature is increased to 90° C. for sulfonation for 12 h, as, the product is filtered and washed with dioxane and then washed with water till neutral, dryed at 80° C., subsequently activated by 0.1 M dilute sulphuric acid for 4 hours, then washed with quantity of water till neutral, finally dryed and at ready.

Example 3

Evaluation of catalytic property and the comparison with traditional catalytic material.

The reaction condition of acetic acid and cyclohexanol esterification: 0.2 g catalyst, 11.5 mL cyclohexanol and 17.5 mL glacial acetic acid are uniformly mixed and then react for 5 h at 100° C., and dodecane is used as internal standard.

The reaction condition of caproic acid and ethanol esterification: 0.3 g catalyst, 6.26 mL caproic acid and 11.67 mL ethanol are uniformly mixed and then react for 5 h at 80° C., and dodecane is used as internal standard.

The reaction condition of dodecanic acid and ethanol esterification: 0.15 g catalyst, 4 mmol dodecanic acid and 50 mL ethanol are uniformly mixed and then react for 5 h at 70° C., and dodecane is used as internal standard.

tures, specific surface area of 600-700 m$^2$/g, an average pore size of 15-23 nm and a pore volume of 0.7-1.4 ml/g, is synthesized by solvothermal method. Said material has a very good swelling property to most of organic solvent comprising benzene and its homologue, alkanes, alcohols and etc. Using this feature in combination with various porous structures and large specific surface area of this material, a new type of stable and highly efficient organic framework solid acid material is successfully synthesized by a new synthesis path following the order of "swelling-sulfonation". Meanwhile, the sulfonated material reserves large specific surface area and various porous structures, the sulfonate content after sulfonation is 2.0-3.5 mmol/g, and the volume of hydrogen ion exchange is 2.2-3.7 mmol/g. The specific surface area is 280-500 m$^2$/g. Compared to aforementioned patents, the solid acid according to the present invention has unique framework hydrophobic property, simple and convenient functionalizing process, better catalytic property and regeneration function.

Table 1 shows the catalytic activity of synthetic sulfonated material in esterification reaction and acylation reaction.

TABLE 1

| Catalyst | acetic acid and cyclohexanol esterification[d] | | caproic acid and ethanol esterification[e] | | dodecanic acid and ethanol esterification[f] | | anisole and acetyl chloride acylation[g] | | |
|---|---|---|---|---|---|---|---|---|---|
| | selective (%) | conversion rate (%) | selective (%) | conversion rate (%) | selective (%) | conversion rate (%) | selective para product (%) | selective ortho product (%) | conversion rate (%) |
| PDVB—SO$_3$H[a] | ~100 | 62.5 | ~100 | 72.5 | ~100 | 89.4 | 97.5 | 2.5 | 61.8 |
| PDVB—SO$_3$H[b] | ~100 | 50.4 | | | | | | | |
| PDVB—SO$_3$H[c] | ~100 | 55.4 | | | | | | | |

[a] 0.2 g catalyst
[b] 0.1 g catalyst
[c] 0.2 g catalyst is recyled 4 times in the catalytic acetic acid and cyclohexanol esterification reaction.
[d] acetic acid and cyclohexanol esterification reaction.
[e] caproic acid and ethanol esterification reaction.

Friedel-Crafts acylation reaction: 0.3 g catalyst, 5.5 mL anisole and 0.71 mL acetyl chloride are uniformly mixed and then react for 5 h at 60° C., and dodecane is used as internal standard.

Table 1 shows the catalytic activity of the material in catalytic esterification and acylation reaction. It can be seen that said material in multiple acid catalytic reactions exhibits good catalytic activity conversion rate, which are 62.5%, 72.5%, 89.4%, 61.8%, respectively. In the catalytic esterification reaction, the activity is reduced by 11.3% after being recycled for 5 times, which indicates that said material has a good regenerating ability and an anti-poisoning ability.

INDUSTRIAL APPLICABILITY

The sulfonate-functionalized mesoporous polypolydivinylbenzene according to the invention has a large specific surface area (523 m$^2$/g).

The sulfonated mesoporous polypolydivinylbenzene material according to the invention has relatively high sulfonate content (2.45 mmol/g).

The sulfonate-functionalized mesoporous polypolydivinylbenzene according to the invention has a stable framework structure (575° C.) and a stable acid site (305° C.).

The sulfonate-functionalized mesoporous polypolydivinylbenzene according to the invention exhibits good catalytic activity and regeneration property in the catalytic esterification and Friedel-Crafts acylation reaction, and the activity is reduced by 11.3% after being recycled for 5 times.

The feature of the present invention is that the polypolydivinylbenzene material, which has various mesoporous struc-

What is claimed:

1. A catalyst of organic framework porous solid acid, wherein said catalyst is effective as a catalyst for catalytic esterification and acylation reactions, wherein the synthesis of said catalyst comprises:

(1) divinyl benzene monomer is added into a mixture solvent of azobisisobutyronitrile, tetrahydrofuran and water, which is stirred for more than 3 hours at ambient temperature and pressure followed by hydrothermal treatment for 1-2 days, then the obtained product is taken out, opened and volatilized at the room temperature to obtain polydivinylbenzene having mesoporous structure;

(2) polydivinylbenzene is ground into 200-mesh powder and degassed for 10 h under nitrogen condition;

(3) polydivinylbenzene blocks are added into 1,1',2-trichloroethane, then the polydivinylbenzene blocks rapidly swell, explode and crack into small blocks accompanied by rapid volume expansion;

(4) 1,1',2-trichloroethane is mixed homogenously with concentrated sulphuric acid with silver sulfate being added as a catalyst, the mixture is then stirred uniformly followed by adding processed polydivinylbenzene obtained from (3) with severe agitation at the temperature of sulfonation for 12 h, the product is filtered and washed with dioxane and then washed with water till neutral, dried at 80° C., subsequently activated by 0.1 M dilute sulphuric acid for 4 hours, then washed with quantity of water until neutral, and finally dried.

2. A catalyst of organic framework porous solid acid according to claim 1 wherein 2 g divinyl benzene monomer is added into a mixture solvent of azobisisobutyronitrile, tetrahydrofuran and water in step (1).

3. A catalyst of organic framework porous solid acid according to claim 1 wherein the divinyl benzene monomer is added into a mixture solvent of 0.03-0.05 g azobisisobutyronitrile, 10-20 milliliter tetrahydrofuran and 1-2 milliliter water in step (1).

4. A catalyst of organic framework porous solid acid according to claim 1 wherein the temperature of hydrothermal treatment is from 75-150° C. in step (1).

5. A catalyst of organic framework porous solid acid according to claim 1 wherein the polydivinylbenzene is 2-3 g in step (2).

6. A catalyst of organic framework porous solid acid according to claim 1 wherein the temperature of degassing treatment under nitrogen condition is from 100-150° C. in step (2).

7. A catalyst of organic framework porous solid acid according to claim 1 wherein 2.0 g polydivinylbenzene blocks are added into 30 milliliter 1,1',2-trichloroethane in step (3).

8. A catalyst of organic framework porous solid acid according to claim 1 wherein 30 milliliter 1,1',2-trichloroethane is mixed homogenously with 70 mL concentrated sulphuric acid with 0.2 g silver sulfate being added as a catalyst in step (4).

9. A catalyst of organic framework porous solid acid according to claim 1 wherein the temperature of sulfonation is 90° C. in step (4).

10. A catalyst of organic framework porous solid acid according to claim 1 wherein the period of sulfonation is 12 h in step (4).

* * * * *